United States Patent
Joshi et al.

(10) Patent No.: US 8,137,708 B2
(45) Date of Patent: Mar. 20, 2012

(54) HERBAL COMPOSITION AND PROCESS FOR ITS PREPARATION

(75) Inventors: Kalpana Sanjay Joshi, Mumbai (IN); Vilas Wagh, Mumbai (IN); Somesh Sharma, Mumbai (IN)

(73) Assignee: Piramal Life Sciences Limited, Mumbai (IN)

( * ) Notice: Subject to any disclaimer, the term of this patent is extended or adjusted under 35 U.S.C. 154(b) by 201 days.

(21) Appl. No.: 12/520,198

(22) PCT Filed: Feb. 20, 2007

(86) PCT No.: PCT/IB2007/050536
§ 371 (c)(1),
(2), (4) Date: Jun. 19, 2009

(87) PCT Pub. No.: WO2008/078203
PCT Pub. Date: Jul. 3, 2008

(65) Prior Publication Data
US 2010/0028472 A1    Feb. 4, 2010

(30) Foreign Application Priority Data
Dec. 21, 2006  (IN) ..................... 2091/MUM/2006

(51) Int. Cl.
*A01N 65/00* (2009.01)

(52) U.S. Cl. ...................................... 424/725
(58) Field of Classification Search .................. None
See application file for complete search history.

(56) References Cited

U.S. PATENT DOCUMENTS

| | | | |
|---|---|---|---|
| 6,852,344 B2 * | 2/2005 | Bandyopadhyay et al. | .. 424/769 |
| 2003/0049334 A1 | 3/2003 | Bandyopadhyay et al. | |
| 2004/0127571 A1 | 7/2004 | Bhalla et al. | |

FOREIGN PATENT DOCUMENTS

JP    2000290165 A  * 10/2000

OTHER PUBLICATIONS

International Search Reports of PCT/IB07/50536 mailed Jul. 31 and Aug. 4, 2008.

* cited by examiner

*Primary Examiner* — Michael Meller
(74) *Attorney, Agent, or Firm* — Westerman, Hattori, Daniels & Adrian, LLP (57) ABSTRACT

A herbal composition comprising a therapeutically effective amount of the extract of *Piper betle* leaves as an active ingredient either alone, or with a pharmaceutically acceptable excipient. A process for the preparation of the herbal composition is provided. The herbal composition is adapted for the treatment of chronic myeloid leukemia (CML; chronic myelogenous leukemia) showing resistance to treatment with imatinib (Gleevec® or Glivec®).

7 Claims, 4 Drawing Sheets

HERBAL COMPOSITION AND PROCESS FOR ITS PREPARATION

FIELD OF THE INVENTION

The present invention relates to a herbal composition comprising a therapeutically effective amount of the extract of *Piper betle* leaves as an active ingredient either alone, or with a pharmaceutically acceptable excipient. The composition of the present invention is adapted for the treatment of chronic myeloid leukemia (CML; chronic myelogenous leukemia) showing resistance to treatment with imatinib (Gleevec® or Glivec®). The present invention also relates to a process for the manufacture of the herbal composition and a method of administering the composition to CML patients showing resistance to imatinib.

BACKGROUND OF THE INVENTION

Chronic myeloid leukemia also known as chronic myelogenous leukemia (hereafter referred to as CML) is a malignant cancer of the bone marrow, which is characterized by increased and unregulated clonal production of predominantly myeloid cells in the bone marrow. According to the National Cancer Institute (NCI) (Chronic Myeloid Leukemia: Treatment: Health Professional Version: General Information 2006), CML is characterized by the reciprocal chromosomal translocation 9:22, which generates the Philadelphia chromosome (Ph). This event occurs in the pluripotent hematopoietic stem cell and transposes the c-abl proto-oncogene on chromosome 9, encoding a protein tyrosine kinase (PTK), to a new position downstream of the second exon of the gene Bcr on chromosome 22. This translocation generates a novel fusion gene, Bcr-Abl, that encodes a chimeric protein, p210Bcr-Abl, the PTK activity of which is aberrantly regulated relative to c-Abl. The Bcr-Abl fusion protein drives a series of inappropriate hemopoietic cell proliferations, and thereby contributes to leukemic transformation (Drucker B J et al; *Chronic myelogenous leukaemia. Hematology. Am. Soc. Hematol. Educ. Program*, 111-135 (2002)). Furthermore, expression of p210Bcr-Abl in transgenic mice has been shown to cause a CML-like myeloproliferative disease. Therefore, p210 Bcr-Abl appears to play a fundamental role as the primary causative factor in CML (Clarkson B D et al; *Leukemia.*: 11:1404-1428 (1997)).

CML progresses in three phases. Most patients are diagnosed in the first phase, called the chronic phase, which has a median duration of 4-6 years. It can develop over time into the second phase called the accelerated phase and eventually to the third phase called the blast phase or blast crisis. In the chronic phase, there are more white blood cells in the blood and the bone marrow than usual. Most are mature cells that can work normally. The disease slowly progresses via an accelerated phase, characterised by the appearance of undifferentiated blast cells (immature white blood cells) in blood, bone marrow and spleen. The accelerated phase then progresses to a terminal blast crisis phase of the disease. In this phase, the median survival is 18 weeks. The blast phase is characterized by the presence of more than 30% of blasts in the blood and bone marrow cells.

The median survival of patients after diagnosis with CML is 4-6 years, with a range of less than one year to more than 10 years (National Cancer Institute: Chronic Myeloid Leukemia: Treatment: Health Professional Version: General Information 2006). Treatment options for patients with CML are limited and are based on the stage of leukemia, and the patient's age and health. The disease may be treated with bone marrow transplant (BMT) therapy or with drug therapy. BMT therapy involves giving very high doses of one or more drugs to the patient to kill most of the cancer cells in the bone marrow and replace the destroyed stem cells with healthy cells from a donor whose tissue type is almost identical with patient's tissue type. However, the use of this treatment is limited by donor availability and treatment related morbidity and mortality. The second treatment option for CML patients is drug therapy. Oral myelosuppressive chemotherapy involving use of hydroxyurea or busulfan has been shown to control blood cell counts and improve symptoms in CML patients, but had poor impact on survival (Hehlmann R et. al.; Blood: 82: 398-407 (1993)). Interferon-alpha has been a therapy of choice for the treatment of CML and has shown improved survival in CML patients. However, there are reports of patients showing resistance to the treatment with Interferon-alpha (Kuhr T et al. *Leuk. Res.* 27(5): 405-411 (2003)). A relatively new drug called imatinib (Gleevec® or Glivec®) is currently the most specific drug for the treatment of CML and is regarded as a very effective therapy. It has already been discussed herein above that the Ph chromosome produces a Bcr-Abl fusion protein, which produces a constitutively active and deregulated protein tyrosine kinase. Gleevec works by inhibiting the Bcr-Abl tyrosine kinase (Buchdunger E. et al; *Biochim. Biophys. Acta* 1551, M11-M18 (2001)). The drug particularly functions through competitive inhibition at the ATP-binding site of the enzyme, which leads to growth arrest or apoptosis in cells that express Bcr-Abl (Radford I R et al; Current Opinion Investigational drugs 3, 492-499 (2002)). The effectiveness of imatinib in CML patients is based on overall hematologic and cytogenetic response rates. Despite significant hematologic and cytogenetic responses, resistance to imatinib has also been observed in CML patients, particularly in patients who have progressed to either the accelerated or blastic phase of the disease. US Patent Application Publication no. 20030158105 ("US'105 Patent Appln.") describes possible mechanisms associated with imatinib resistance in CML patients and discloses a number of Bcr-Abl mutants associated with resistance to imatinib. Attempts have been made to find new therapeutic strategies to prevent or overcome this resistance. Recently, two experimental drugs namely nilotinib (AMN-107) and dasatinib (BMS-354825) were found to be effective in circumventing some but not all forms of imatinib resistance. Nilotinib was found to be effective for the treatment of CML patients; however, patients with T315I mutations were resistant to this drug (Bocchia M et al: Emerging drugs in CML; *Expert Opin. Emerging Drugs* (2006) 11(4): 651-664). The T315I mutant is one of the more predominant mutations seen in imatinib-resistant patients. This T315I mutation was shown to preserve kinase activity resulting in ineffective binding of imatinib to Bcr-Abl. Another drug, ON-0122380 which is in the preclinical stage has been found to inhibit both wild-type and T315I imatinib resistant mutant, however, safety and efficiency of this drug in preventing the appearance of imatinib resistance is yet to be evaluated as it has still not entered clinical trial. However, despite these developments, there still exists a continuing need for agents which are effective against the imatinib-resistant CML.

The present inventors have worked extensively to find a solution to the problem of CML patients showing resistance to treatment with imatinib. The present inventors unexpectedly found that a composition containing extract of *Piper betle* leaves exhibits potent antiproliferative activity against Bcr-Abl mutated cell lines which are resistant to imatinib. The present invention is advantageous in that the herbal composition can be obtained by a simple manufacturing method.

SUMMARY OF THE INVENTION

In one aspect, the present invention is directed to a herbal composition comprising a therapeutically effective amount of an extract of *Piper betle* leaves either alone, or with at least one pharmaceutically acceptable excipient, which composition is adapted for use in the treatment of imatinib-resistant chronic myeloid leukemia (CML).

In another aspect, the present invention is directed to a herbal composition comprising a therapeutically effective amount of an extract of *Piper betle* leaves along with at least one pharmaceutically acceptable excipient, wherein the composition is advantageous in terms of higher level of safety when adapted for use in the treatment of imatinib-resistant chronic myeloid leukemia (CML).

In another further aspect, the present invention is directed to a composition comprising a therapeutically effective amount of the extract of *Piper betle* leaves either alone or with at least one pharmaceutically acceptable excipient for use in the treatment of imatinib-resistant chronic myeloid leukemia (CML), wherein the resistance to imatinib is caused by Bcr-Abl mutation.

In yet another aspect, the present invention is directed to a process for the manufacture of the herbal composition comprising a therapeutically effective amount of the extract of *Piper betle* leaves along with at least one pharmaceutically acceptable excipient.

In yet another further aspect, the present invention is directed to a method for the administration of the composition of the present invention, adapted for the treatment of imatinib-resistant chronic myeloid leukemia.

In another further aspect, the present invention is directed to a composition comprising a therapeutically effective amount of the extract of *Piper betle* leaves as an active ingredient, either alone, or along with at least one pharmaceutically acceptable excipient, wherein said composition is formulated for oral, parenteral, intraperitonial, subcutaneous, intravenous or intraarticular administration.

In another further aspect, the present invention is directed to a method for the treatment of imatinib-resistant chronic myeloid leukemia comprising administering to a patient in need of such a treatment a therapeutically effective amount of the herbal composition.

In yet another further aspect, the present invention is directed to use of the herbal composition for the manufacture of a medicament for the treatment of imatinib-resistant chronic myeloid leukemia.

DETAILED DESCRIPTION OF THE INVENTION

The present invention is based on the finding that a herbal composition comprising a therapeutically effective amount of the extract of *Piper betle* leaves as an active ingredient is effective against the Bcr-Abl mutated imatinib-resistant cell lines and hence, is a significant invention in the art of cancer particularly leukemia. More particularly, the present invention is noteworthy in that it provides a solution to override the recent emergence of resistance to imatinib, a revolutionary drug for the treatment of CML, the otherwise dreadful disease.

The following is a list of definitions for terms used herein. These definitions apply to the terms as they are used throughout the specification unless otherwise limited in specific instances.

The term "pharmaceutically acceptable" as used herein means that the excipient, diluent, and/or its salt must be compatible with the other ingredients of the formulation, and not deleterious to the recipient thereof.

The term "pharmaceutically acceptable excipient" as used herein means a non-toxic, inert solid, semi-solid, diluent, encapsulating material or formulation auxiliary of any type. Some examples of materials which can serve as pharmaceutically acceptable excipients are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

The term, "therapeutically effective amount" as used herein means an amount of the composition (e.g., the extract of *Piper betle* leaves) sufficient to significantly induce a positive modification in the condition to be regulated or treated, but low enough to avoid side effects, if any (at a reasonable benefit/risk ratio), within the scope of sound medical judgment. The therapeutically effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable excipient utilized, and like factors.

The terms "extract of *Piper betle* leaves" and "*Piper betle* leaf extract" are used interchangeably.

The terms "extract" or "the extract" as used herein, refers to the extract of *Piper betle* leaves. The term extract or the extract of *Piper betle* leaves means a blend of compounds present in the leaves of the plant *Piper betle*. The extract is prepared using extraction procedures well known in the art (e.g., the use of organic solvents such as lower alcohols, alkyl esters, alkyl ethers, alkyl ketones, chloroform, petroleum ether, hexane and/or inorganic solvents such as water).

The terms "herbal composition" or "composition" are used interchangeably and may refer to a composition comprising therapeutically effective amount of the extract of *Piper betle* leaves either alone or with at least one pharmaceutically acceptable excipient. The term "either alone" may further indicate that the composition contains only the extract of *Piper betle* leaves without any pharmaceutically acceptable excipient added therein.

As used herein, the term "about" refers to a range of values ±20% of a specified value. For example, the phrase "about 20" includes ±20% of 20, or from 16 to 24.

As used in the specification and the appended claims, the singular forms "a," "an," and "the" include plural referents unless the content clearly dictates otherwise. *Piper betle* L is a botanical name of the plant, betel vine. The heart shaped green leaf of the *Piper betle* plant is popularly known as paan in India. *Piper betle* belongs to the family of Piperaceae i.e. the Black Pepper family (Gunther E.: *The Essential oils*, 5:160-161 (1952)). The leaf of the *Piper betle* plant is also commonly called the betel leaf. Use of *Piper betle* extract (herein after referred to as "the extract") for the treatment of various diseases is reported: Japanese published Patent Applns. JP 2001098267 discloses use of the extract as an antioxidant; JP 2002212086 discloses that the extract has excellent antibacterial activity; JP 9278666 teaches that the extract can be used for sterilizing microorganisms in oral cavity and for removing effects on causes of dental caries; JP 200130685 reports use of the extract as an antiallergic agent; PCT Published Patent Appln. WO 0245730 discloses use of the extract for its anti-monocytic activity; WO 0245731 teaches the usefulness of the extract for the treatment of visceral leishmaniasis or kala-azar and U.S. Pat. No. 6,967,034 teaches use of the extract in the treatment of CD33+ acute and chronic myeloid leukemia.

The present invention relates to a herbal composition comprising as an active ingredient the extract of *Piper betle* leaves either alone or with a pharmaceutically acceptable excipient.

The betel (*Piper betle*) leaf is selected from the following types namely Wild type, Climber type, Bangla type and Sweet type.

In one aspect, the herbal composition according to the present invention comprises a therapeutically effective amount of the extract of *Piper betle* leaves ("the extract") as an active ingredient either alone or along with at least one pharmaceutically acceptable excipient.

The therapeutic amount of the extract to be included in the composition varies between about 5% and about 50% (w/w) based on the total weight of the composition.

The composition of the present invention may be prepared by any of the methods well known in the art of pharmacy. All methods include the step of bringing the active ingredient i.e. the extract into association with an appropriately selected pharmaceutically acceptable excipient. Actual methods for preparing administrable compositions and adjustments necessary for administration to subjects will be known or apparent to those skilled in the art and are described in more detail in, for example, "Remington: The Science And Practice Of Pharmacy," Gennaro, A., Lippincott, Williams & Wilkins, Philadelphia (2000) (formerly "Remingtons Pharmaceutical Sciences").

According to one aspect of the present invention, there is provided a process for the preparation of the herbal composition comprising the steps of:
(a) preparing an extract of the *Piper betle* leaves;
(b) mixing the extract of step (a) with at least one pharmaceutically acceptable excipient to obtain the composition.

The extract of *Piper betle* leaves to be used according to the invention is prepared by conventional methods of extraction. The general procedure for the preparation of the *Piper betle* leaf extract is described herein below.

The herbal composition of the present invention may be formulated for oral administration by compounding the active ingredient i.e. the extract with the usual non-toxic pharmaceutically acceptable excipients for tablets, pellets, granules, capsules, solutions, emulsions, suspensions, and any other form suitable for use. Formulations of the present invention encompass those which include talc, water, glucose, lactose, gum acacia, gelatin, mannitol, starch paste, magnesium trisilicate, corn starch, keratin, colloidal silica, potato starch, urea, and other excipients suitable for use in manufacturing preparations, in solid, semisolid or liquid form and in addition auxiliary, stabilizing, thickening and coloring agents may be used. For preparing solid compositions such as tablets or capsules, the extract is mixed with a pharmaceutical excipient (e.g., conventional tableting ingredients such as corn starch, lactose, sucrose, sorbitol, talc, stearic acid, magnesium stearate, dicalcium phosphate or gums) and other pharmaceutical diluents (e.g., water) to form a solid composition. This solid composition is then subdivided into unit dosage forms containing an effective amount of the composition of the present invention. The tablets or pills containing the extract can be coated or otherwise compounded to provide a dosage form affording the advantage of prolonged action. For example, the tablet or pill can comprise an inner dosage, and outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings such materials including a number of polymeric acids and mixtures of polymeric acids with such materials as shellac, cetyl alcohol, and cellulose acetate.

The liquid forms, in which the extract may be incorporated for administration orally or by injection, include aqueous solution, suitably flavored syrups, aqueous or oil suspensions, and flavored emulsions with edible oils as well as elixirs and similar pharmaceutical vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin. Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The composition of the present invention containing the extract of *Piper betle* leaves may also be formulated for parenteral administration by injection, which includes using conventional catheterization techniques or infusion. Formulations for injection may be presented in unit dosage form, e.g., in ampules, or in multi-dose containers, with an added preservative. Alternatively, the active ingredients may be in powder form for reconstitution with a suitable vehicle, e.g., sterile pyrogen-free water, before use. Aqueous injection suspensions may contain substances which increase the viscosity of the suspension including, for example, sodium carboxymethyl cellulose, sorbitol, and/or dextran. Optionally, the suspension may also contain stabilizers. Liposomes can also be used to encapsulate the agent for delivery into the cell.

In practicing this invention, the composition comprising the extract of *Piper betle* leaves as an active ingredient may be used alone or in combination with other therapeutic agents. In certain embodiments, the composition of this invention may be co-administered along with other drugs typically prescribed for cancer chemotherapy according to generally accepted medical practice.

In accordance with the present invention, the desirable dose of the composition varies depending on the condition and the weight of the subject, severity, drug form, route and period of administration, and can be readily determined by a skilled medical practitioner. However, in order to obtain desirable effects, it is generally recommended to administer the composition according to this invention at a dosage ranging from 1 g to 20 g per day in a single dosage form or a separate multi-dosage form.

According to the present invention, the herbal composition is adapted for use in the treatment of imatinib-resistant chronic myeloid leukemia (CML). It has been established by experimental results that the composition of the present invention can be used effectively for the treatment of imatinib-resistant CML. Not only is the composition easier to prepare but also it provides a superior alternative to existing expensive drugs, surgery, or both. More importantly, the composition is free of serious adverse reactions that are caused by commonly used anticancer drugs.

The present invention contemplates within its scope a method for the treatment of imatinib-resistant chronic myeloid leukemia comprising administering to a patient in need of such a treatment a therapeutically effective amount of the herbal composition.

According to the present invention, in a method for the treatment of imatinib-resistant chronic myeloid leukemia, it is recommended to administer the composition at a dosage ranging from 1 g to 20 g per day in a single dosage form or a separate multi-dosage form.

The efficacy of the herbal composition of the present invention was evaluated by the inventors in an in vitro study whereby it was observed that the composition of the present invention has potent inhibitory activity against Bcr-Abl mutated imatinib-resistant cell lines. More interestingly, it also showed potent antiproliferative activity against the cell line, which expresses human Bcr-Abl/T315I, the most commonly observed mutated form of Bcr-Abl which is imatinib resistant. This is an outstanding advancement in the art because the Bcr-Abl/T315I mutation has shown resistance to the two most promising experimental drugs nilotinib (AMN-107) and dasatinib (BMS-354825). This kept the challenge open to the scientists in the field to provide a solution to this problem. The present inventors have provided a practical solution to this problem in the form of a herbal composition comprising a therapeutically effective amount of the extract of *Piper betle* leaves.

Figure 1:
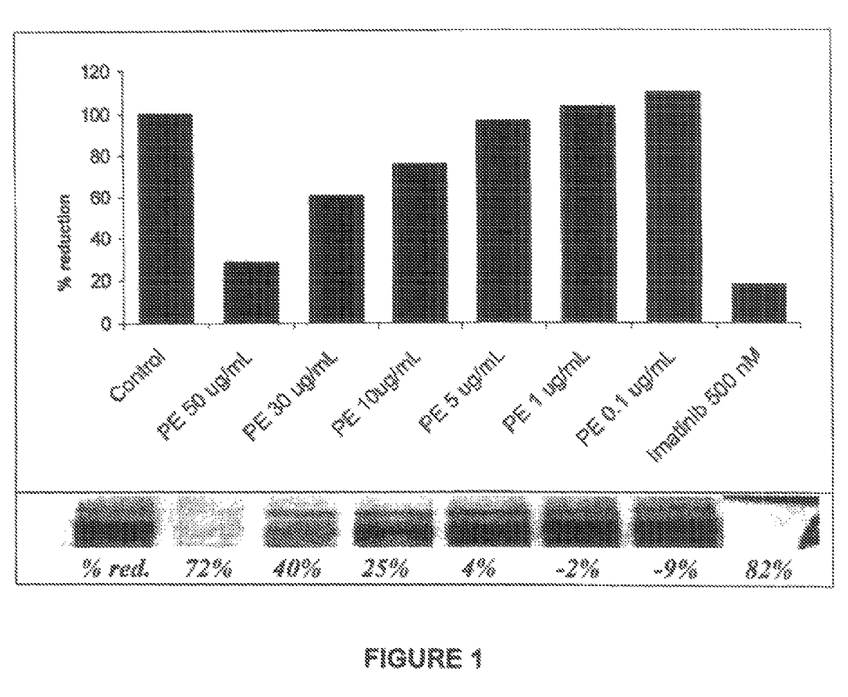
FIG. 1 illustrates in vitro activity of the extract of *Piper betle* leaves against K-562 cell line demonstrating the Bcr-Abl kinase inhibitory activity of the extract.

In an in vitro efficacy testing on Bcr-Abl/Wild type (Bcr-Abl/WT) positive K-562 cell line (an erythroleukemia cell line derived from a chronic myeloid leukemia patient), the inventors observed that the composition of the present invention comprising the extract of *Piper betle* leaves is a direct inhibitor of Bcr-Abl tyrosine kinase as seen in autophosphorylation studies as indicated in FIG. 1. The composition showed a dose dependent significant inhibition of kinase activity in K-562 cell line.

The inventors tested the effect of the composition on five clinically observed imatinib-resistant cell lines in comparison with imatinib. It was observed that the composition potently inhibits the mutated imatinib-resistant cell lines. The results of this study are described in detail herein below. The results depicted in Table 4 indicate that the dose of the composition remains consistent as against the dose of imatinib, which varies drastically.

Figure 3A:
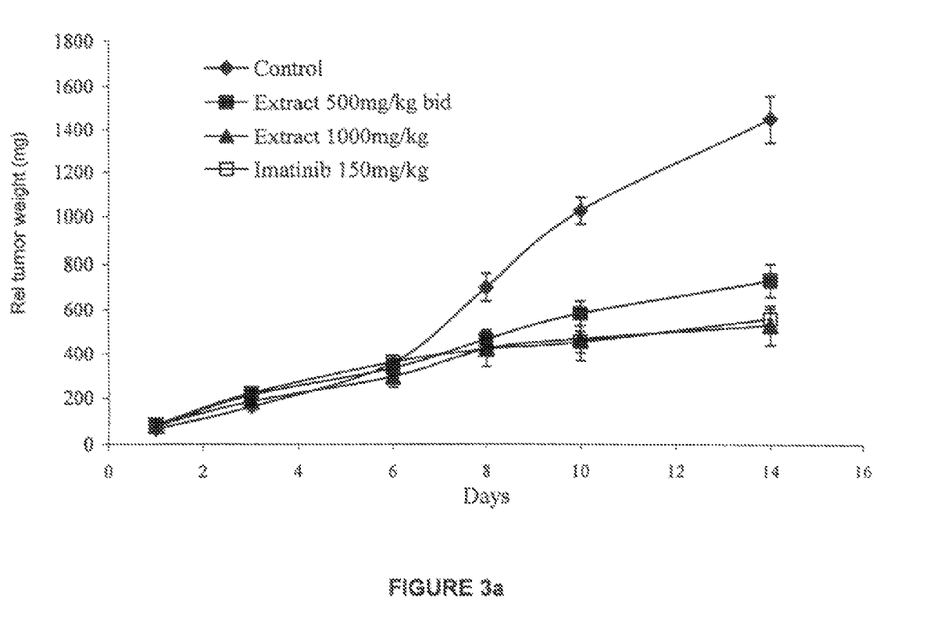
FIG. 3a illustrates that the extract of *Piper betle* leaves exhibits in vivo efficacy against wild type Ba/F3 Bcr-Abl/p210 WT xenograft model in SCID mice equivalent to imatinib (SET I)

To demonstrate efficacy of the composition of the present invention, the inventors tested the extract of *Piper betle* leaves for its in vivo antitumor efficacy using cell lines Ba/F3 transfectants expressing full length wild type Bcr-Abl and mutated Bcr-Abl/T315I cells in xenograft models of SCID mice. It was observed that the extract of *Piper betle* leaves shows significantly greater in vivo efficacy than imatinib in inhibiting the most predominant mutated form of Bcr-Abl i.e. T315I when tested at the same doses as that of wild type Bcr-Abl expressing xenograft i.e. BAF3 Bcr-Abl/p210 WT. It is evident from the graphical presentation in FIGS. 3a and 3b that the doses at which the extract is effective against the wild type Bcr-Abl xenograft is consistent with the doses at which the extract is effective against the mutated T315I xenograft also. On the contrary, imatinib exhibited significant activity against wild type Bcr-Abl xenograft but at the same dose it was found to be inactive against the mutated T315I xenograft models.

In addition, the *Piper betle* extract also exhibited antiproliferative activity against other human leukemic cell lines such as HL-60 and Molt-4.

The present invention will be more readily understood by referring to the following examples which are given to illustrate the invention rather than to limit its scope.

EXAMPLES

Example 1

General Procedure for the Preparation of the Extract of *Piper betle* Leaves

The leaves of the *Piper betle* plant are dried under shade, avoiding direct sunlight. The leaves are ground to obtain powder having %-mesh particle size using an appropriate mill. About 100 Kgs. of the powder is taken in a suitable reaction vessel and 8 times of the solvent (80% alcohol) is added to it. The powder of the leaves is soaked in the solvent mixture for 1 hour with frequent stirring. The contents are extracted using suitable heating device (steam) using reflux mechanism with continuous stirring at 70° C. 5° C. for 4 hours (after temperature attainment). The contents are then cooled to room temperature and filtered using either a centrifuge, a filter press, a sieve or a nylon cloth to obtain a clear filtrate. The marc is removed and the filtrate is preserved. The process is repeated with marc which is removed after filtration. The extracts are combined and processed for solvent recovery. The clear filtrate is transferred to same reaction vessel and concentrated by distillation with solvent recovery at 70° C.±5° C. and 25 mm±5 mm vacuum, to obtain soft extract having honey-like consistency. This soft extract may contain minimum to negligible amount of alcohol. The resulting soft extract is then transferred to a suitable vacuum oven and the contents are dried at 70° C.±5° C. with 25 mm±5 mm vacuum to obtain a thick paste. The solvents (water and alcohol) are completely removed from the extract. The extract can be stored at 25° C./40% relative humidity (RH).

Example 2

Preparation of the Herbal Composition Containing the Extract of *Piper betle* Leaves: Preparation of Granules The composition contains ingredients listed in the following Table 1 in the quantity specified therein.

TABLE 1

| Ingredient | Quantity (1 gm) |
|---|---|
| Extract of *Piper betle* leaves | 0.4500 |
| Mannitol | 0.4000 |
| Aerosil | 0.0500 |
| Citric acid monohydrate | 0.0500 |
| Sodium methyl paraben | 0.0020 |
| Sodium propyl paraben | 0.0002 |
| Sodium benzoate | 0.0020 |
| Bronopol | 0.0002 |
| Raspberry flavour | 0.0100 |
| Sugar caramel colour | 0.0100 |
| Aspartame | 0.0150 |
| Menthol | 0.0100 |
| Isopropyl alcohol | q.s. |

Step 1:
The ingredients: extract of *Piper betle* leaves, mannitol and isopropyl alcohol were weighed in the specified quantity (as mentioned in the above Table 1) in a suitable container. The ingredients were mixed homogeneously to obtain a suspension. The suspension was further dried by fluidized bed drying process.

Step 2:
The ingredients: aerosil, citric acid monohydrate, sodium methyl paraben, sodium propyl paraben, sodium benzoate, bronopol, raspberry flavour, sugar caramel colour, aspartame and menthol were weighed in the specified quantity (as mentioned in the above table) in a suitable container. The contents were mixed thoroughly and passed through a sieve of 40 mesh size. The mixture was then uniformly blended.

Step 3:
The suspension from step 1 and the blended mixture from step 2 were mixed together to obtain granules and filled in a pouch.

The pouch that is used for filling the granules may have the following specification.

Laminated material Glassine paper (40 gsm/Aluminium (9 μm/Poly (150 gauge)
Type of Pouch Gusseted
Dimension: 70×70 mm+2 mm
Sealing: 5 mm±1 mm on all three sides and 5 mm±1 mm on fourth side on filling
Weight: 1.200 gms±0.100 gms.

Example 3

Preparation of the Herbal Composition Containing the Extract of *Piper betle* Leaves: Preparation of Suspension The composition contains ingredients listed in the following Table 2 in the quantity specified therein.

TABLE 2

| Ingredients | Quantity of Pablocan Syrup (5 ml) |
|---|---|
| Extract of *Piper betle* leaves | 1.0000 |
| Sodium methyl paraben | 0.0100 |
| Sodium propyl paraben | 0.0025 |
| Sodium benzoate | 0.0100 |
| Bronopol | 0.0025 |
| Mannitol powder | 1.0000 |
| Propylene glycol | 1.0000 |
| Aspartame | 0.0050 |
| Raspberry flavour | 0.0063 |
| Citric acid | 0.0500 |
| Menthol | 0.0500 |
| Sodium Carboxymethylcellulose (sodium CMC) | 0.0250 |
| Demineralised (DM) water | q.s. |

Step 1:
The ingredients propylene glycol, mannitol, raspberry flavour and menthol were accurately weighed in the specified quantity (as mentioned in table 2), in a suitable container. The ingredients were mixed homogeneously with constant stirring to obtain a suspension.

Step 2:
The ingredients sodium methyl paraben, sodium propyl paraben, sodium benzoate, bromerol, demineralised water and citric acid were accurately weighed in the specified quantity (as mentioned in the above table 2), in a suitable container. The ingredients were mixed thoroughly to obtain a solution.

Step 3:
The ingredients sodium CMC and DM Water were accurately weighed in the specified quantity (as mentioned in the above table), in a suitable container. The ingredients were mixed well with constant stirring to obtain a gel.

Step 4:
The ingredients aspartame and DM Water were accurately weighed in the specified quantity (as mentioned the above table), in a suitable container. The ingredients were mixed thoroughly to obtain a solution.

Step 5:
The ingredients: the extract of *Piper betle* leaves, sugar caramel colour and DM water were accurately weighed in the specified quantity (as mentioned the above table), in a suitable container. The ingredients were mixed homogeneously with constant stirring to obtain a suspension.

Step 6:
All the above contents resulted from Steps 1 to 5 were mixed homogeneously and filled into an amber coloured bottle.

Example 4

Determination of In Vitro Antiproliferative Activity of the Extract

Cell Proliferation Assay:
Seven hematopoietic cell lines were procured from different sources, the details of which are provided in the following Table 3. These cell lines were maintained under optimum conditions of growth as suggested by the suppliers.

TABLE 3

Description of various hematopoietic cell lines

| Sr. No | Cell line | Source | Ph status | Medium of propagation (FBS %) |
|---|---|---|---|---|
| 1 | Ba/F3 Bcr-Abl p210 WT | OHSU | +ve wild type | RPMI-1640 (10%) |
| 2 | Ba/F3 Bcr-Abl T315I | OHSU | +ve mutated | RPMI-1640 (10%) |
| 3 | Ba/F3 Bcr-Abl E255K | OHSU | +ve mutated | RPMI-1640 (10%) |
| 4 | Ba/F3 Bcr-Abl H396P | OHSU | +ve mutated | RPMI-1640 (10%) |
| 5 | Ba/F3 Bcr-Abl M351T | OHSU | +ve mutated | RPMI-1640 (10%) |

TABLE 3-continued

Description of various hematopoietic cell lines

| Sr. No | Cell line | Source | Ph status | Medium of propagation (FBS %) |
|---|---|---|---|---|
| 6 | Ba/F3 Bcr-Abl F359V | OHSU | +ve mutated | RPMI-1640 (10%) |
| 7 | Ba/F3* | OHSU | −ve wild type | IMDM (10%) + IL3 |
| 8 | K-562 | ATCC | +ve wild type | IMDM (10%) |

*Ba/F3 cells containing vector only (Ba/F3-pSR) and FBS refers to fetal bovine serum
Sources: OHSU: Oregon Health Sciences University, USA
ATCC: American Type culture collection, USA The cell lines described in Table 3 were used to test the antiproliferative activity of the extract of *Piper betle* leaves. The potential of the extract as an anti-proliferative agent was compared with imatinib in imatinib-resistant cell lines using $^3$H-Thymidine uptake assay.

The $^3$H-Thymidine-incorporation is a method used for cell proliferation assay. $^3$H-Thymidine-incorporation is directly proportional to the number of dividing cells in culture.

Method

Cells were seeded at a density of 3 to $5 \times 10^3$ per well (in 0.09 mL volume) in a transparent 96 well tissue culture plate (NUNC, USA) and allowed to incubate at 37° C. in 5% $CO_2$ incubator for 2-6 h. Imatinib was purchased from Natco Pharma, India. A 10 mmol/L stock solution of imatinib in DMSO was prepared and experiments were done with dilutions of the stock solution. The extract and imatinib were diluted in a suitable medium at various concentrations, and 0.01 mL of 10× stocks were added to each well in triplicate. Plates were incubated at 37° C. in 5% $CO_2$ incubator for 72 h, with an intermittent microscopic observation every 24 h. After 72 h incubation, plate was centrifuged at 1000 rpm for 10 minutes in a plate centrifuge. The supernatant was carefully aspirated and $^3$H-Thymidine was added to all the wells at a concentration of 0.5 µCi/well in 0.100 mL complete medium. Plates were further incubated at 37° C. in 5% $CO_2$ incubator for 6-14 h. At the end of incubation period, cells from 96 well plates were harvested with the help of a cell harvester (Packard, USA) on 96 well glass-filter plate (Cat # 6005177, Unifilter-96, GF/B, Packard, USA). The filter plate was dried completely at 60° C. for 1 h or overnight at room temperature. After drying, the bottom of the plate was blocked with a seal and 0.05 mL/well of scintillant fluid (Microscint-O, Packard) was added to it. The plate was sealed from top, read on Scintillation counter (TopCount, Packard) and percent inhibition and $IC_{50}$ were calculated in comparison with control values. The results are provided in the following Table 4.

TABLE 4

In-vitro activity of the extract of *Piper betle* leaves against the Bcr-Abl wild type and mutated imatinib-resistant cell lines

| Sr No | Cell lines | Extract of *Piper betle* leaf ($IC_{50}$) µg/mL | Imatinib ($IC_{50}$) µM |
|---|---|---|---|
| 1 | Ba/F3 Bcr-Abl P210 | 20.0 | 0.5 |
| 2 | Ba/F3 Bcr-Abl T315I | 8.5 | 30.0 |
| 3 | Ba/F3 Bcr-Abl E255K | 15.0 | >30 |
| 4 | Ba/F3 Bcr-Abl H396P | 11.0 | 2.1 |
| 5 | Ba/F3 Bcr-Abl M351T | 7.5 | 11.0 |
| 6 | Ba/F3 Bcr-Abl F359V | 7.0 | 2.8 |
| 7 | K-562 | 15.0 | 0.3 |

It is evident from the results depicted in the above Table 4 that the extract of *Piper betle* leaves exhibited significant antiproliferative activity against the Bcr-Abl mutated imatinib-resistant cell lines (T315I, E255K, H396P, M351T and F359V). It is also notable from the presented data that the $IC_{50}$ value for the composition of the present invention is consistent whereas the $IC_{50}$ value for imatinib varies considerably.

Example 5

Determination of Cytotoxicity of the Extract of *Piper betle* Leaves in Additional Bcr-Abl Mutated Imatinib-Resistant Cell Lines

TABLE 5

Description and growth conditions of additional Bcr-Abl mutated imatinib-resistant cell lines

| Sr No | Cell line | Source | Ph status | Medium of propagation (FBS %) |
|---|---|---|---|---|
| 1 | Ba/F3 Bcr-Abl/E255V | OHSU | +ve wild type | RPMI-1640 (10%) |
| 2 | Ba/F3 Bcr-Abl/F317V | OHSU | +ve mutated | RPMI-1640 (10%) |
| 3 | Ba/F3 Bcr-Abl/H396R | OHSU | +ve mutated | RPMI-1640 (10%) |
| 4 | Ba/F3 Bcr-Abl/M284V | OHSU | +ve mutated | RPMI-1640 (10%) |
| 5 | Ba/F3 Bcr-Abl/Q252H | OHSU | +ve mutated | RPMI-1640 (10%) |
| 6 | Ba/F3 Bcr-Abl/Y253F | OHSU | +ve mutated | RPMI-1640 (10%) |
| 7 | Ba/F3 Bcr-Abl/Y253H | OHSU | +ve wild type | RPMI-1640 (10%) |

Source of imatinib-resistant cell lines: All the cell lines are procured from Dr. Brian Druker's laboratory, Howard Hughes Medical Institute, Oregon Health and Science University Cancer Institute, Portland, Oregon, USA Cytotoxicity Assay Cell counting kit-8 (CCK-8) was used to study cytotoxicity of the extract. The CCK-8 allows very convenient assays by utilizing Dojindo's highly water-soluble tetrazolium salt. WST-8 [2-(2-methoxy-4-nitrphenyl)-3-(4-nitrophenyl)-5-(2, 4-disulfophenyl)-2H-tetrazolium, monosodium salt]) produces a water-soluble formazan dye upon reduction in the presence of an electron mediator.

Cells were seeded at a density of 3 to $5 \times 10^3$ per well (in 0.09 mL volume) in transparent 96 well tissue culture plate (NUNC, USA) and allowed to incubate at 37° C. in 5% $CO_2$ incubator for 2-6 h. Samples were diluted in a medium at various concentrations, and 0.01 mL of 10× stocks were added to each well in triplicate. Plates were incubated at 37° C. in 5% $CO_2$ incubator for 72 h, with an intermittent microscopic observation every 24 h. After 72 h incubation, 10 µL CCK-8 solution was added to each well, and plates were further incubated in same incubation conditions for 4 h, followed by spectrophotometeric absorbance at 450 nm on a plate reader. The results are presented in the following Table 6.

TABLE 6

Effect of the extract of *Piper betle* leaves on cytotoxicity of various Bcr-Abl wild type and mutated imatinib-resistant cell lines

| Sr. No. | Imatinib-sensitive or resistant status | Cell lines | Imatinib IC$_{50}$ µM | R/S ratio | Extract of *Piper betle* leaves IC$_{50}$ µg/mL | R/S ratio |
|---|---|---|---|---|---|---|
| 1 | sensitive | Ba/F3 Bcr-Abl/WT | 0.9 | 1 | 7.4 | 1 |
| 2 | resistant | Ba/F3 Bcr-Abl/T315I | 20.8 | 23.1 | 5.6 | 0.76 |
| 3 | resistant | Ba/F3 Bcr-Abl/E255K | 10.0 | 11.1 | 5.2 | 0.70 |
| 4 | resistant | Ba/F3 Bcr-Abl/E255V | 13.6 | 15.1 | 5.8 | 0.78 |
| 5 | resistant | Ba/F3 Bcr-Abl/F317V | 2.4 | 2.7 | 5.0 | 0.68 |
| 6 | resistant | Ba/F3 Bcr-Abl/F359V | 3.8 | 4.2 | 7.9 | 1.07 |
| 7 | resistant | Ba/F3 Bcr-Abl/H396P | 1.6 | 1.8 | 4.4 | 0.59 |
| 8 | resistant | Ba/F3 Bcr-Abl/H396R | 2.8 | 3.1 | 4.6 | 0.62 |
| 9 | resistant | Ba/F3 Bcr-Abl/M284V | 4.6 | 5.1 | 5.0 | 0.68 |
| 10 | resistant | Ba/F3 Bcr-Abl/M315T | 2.2 | 2.4 | 5.0 | 0.68 |
| 11 | resistant | Ba/F3 Bcr-Abl/Q252H | 4.9 | 5.4 | 6.6 | 0.89 |
| 12 | resistant | Ba/F3 Bcr-Abl/Y253F | 8.6 | 9.6 | 9.6 | 1.30 |
| 13 | resistant | Ba/F3 Bcr-Abl/Y253H | 14.3 | 15.9 | 5.0 | 0.68 |

R/S = Resistance vs sensitivity ratio

It is evident from the results specified in the above Table 6 that imatinib was less active in all the imatinib-resistant Bcr-Abl mutated cell lines as compared to wild type cell line. Whereas the extract of *Piper betle* leaves exhibited significant activity against all the resistant Bcr-Abl mutated cell lines.

Example 6

Effect of the Extract of *Piper betle* Leaves on Bcr-Abl Kinase Activity Bcr-Abl Kinase Assay For this purpose, the Bcr-Abl tyrosine kinase from K-562 cell lysate was immunoprecipitated. These immune complexes were used for kinase reaction using $^{32}$P-ATP and are further characterized on SDS-PAGE (Sodium dodecyl sulphate (SDS) polyacrylamide electrophoresis) followed by autoradiography.

K-562 cells were harvested after the incubation with or without the extract by centrifugation at 1000 rpm for 10 minutes. Cells were lysed using 0.2 mL of cell lysis buffer (CelLytic™ M Cell lysis Reagent, SIGMA) on ice. The lysate was centrifuged at 10,000 g for 30 minutes at 4° C. and supernatant was collected. Protein was estimated using Bradford method of protein estimation. In 200-400 µg of protein 3 µg of monoclonal antibody against c-abl was added and incubated at 4° C. for 1 to 2 h. To this 3-5 µl (1:1 slurry) of protein A-sepharose: dilution buffer per µg monoclonal antibody was added and further kept at 4° C. for overnight. Centrifuged and beads washed with 0.5 ml of kinase assay buffer (Kinase assay buffer: 50 mM HEPES (pH 7.5), 1 mM DTT, 2.5 mM. EGTA, 10 mM β-glycerophosphate, 1 mM NaF, 10 mM MgCl$_2$) twice. Beads coated with Bcr-Abl protein were resuspended in 30 µl of kinase buffer. Kinase assay was performed using $(\gamma)^{32}$P-ATP in 4× Phosphatase inhibitor (PI) for 30-40 minutes at room temperature. This reaction mixture was subjected to SDS-PAGE and detected by autoradiography. The dose dependent inhibition of Bcr-Abl kinase activity in Bcr-Abl+ve K-562 cells exhibited by the extract of *Piper betle* leaves after 24 hours is demonstrated in FIG. 1.

Example 7

Figure 2:
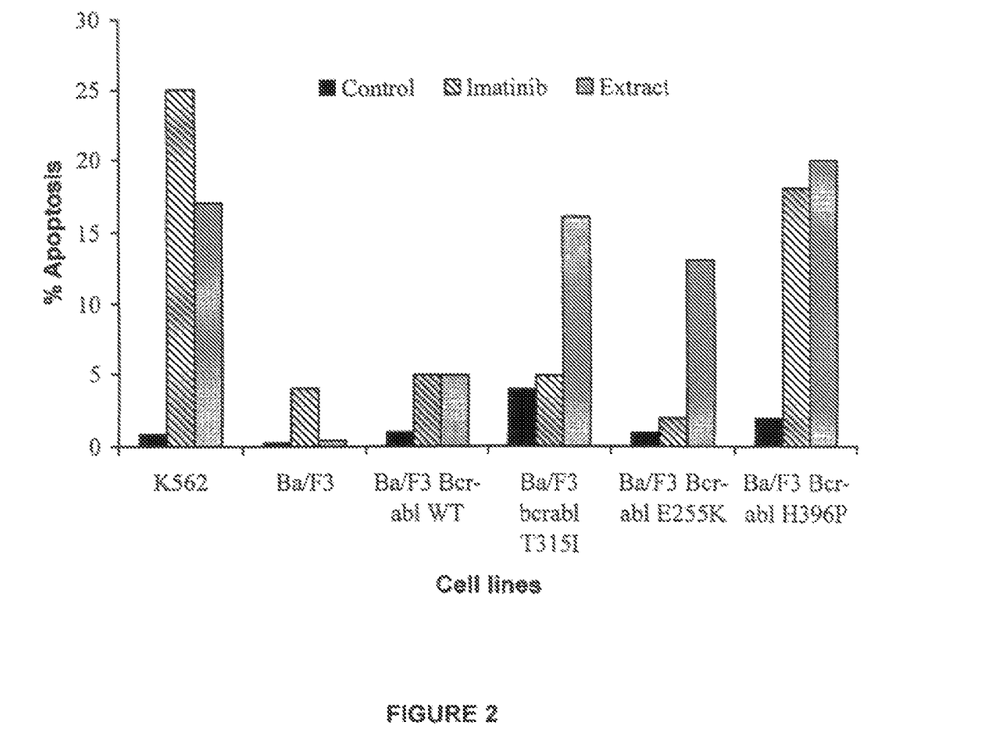
FIG. 2 illustrates apoptosis induced by the extract of *Piper betle* leaves in Bcr-Abl mutated imatinib-resistant cell lines.

Effect of the Extract of *Piper betle* Leaf in Bcr-Abl Mutated Imatinib-Resistant Cell Lines on Cell Cycle and Apoptosis Using Flow Cytometry Cells for flow cytometery were seeded at a density of 10×10$^4$ cells/mL and incubated with the extract/imatinib for 24 h at 37° C. in 5% CO$_2$ incubator. At the end of incubation, cells were harvested by centrifugation at 1000 rpm for 10 minutes, followed by 2 washes with phosphate buffered saline (PBS). Cell pellet from the last wash was gradually resuspended in 70% ice-cold ethanol that facilitates the permeablisation of stains. Cell suspension was stored for a minimum period of 4 h before staining with propidium iodide (PI). Fixed cells were stained with PI (80 µg/mL) in presence of RNase A (50 µg/mL), and read on BD FACS caliber for cell cycle analysis. The results of this study are presented in FIG. 2 which clearly indicate that apoptosis induced by the extract of *Piper betle* leaves in imatinib-resistant cell lines is significant.

Example 8

Efficacy of the Extract of *Piper betle* Leaves in Chronic Myleogenous Leukemia (CML) Patient Cells All samples were obtained with informed consent and with the approval of the ethical committee. Diagnosis of CML disorder used in this study was based on standard morphologic, immunophenotypic, and cytogenetic criteria. Blood cells were subjected to Ficoll-hypaque density gradient centrifugation, followed by collection of buffy-coat.

CML samples were procured from Nizam's Institute of Medical Sciences, Hyderabad. The sample was transported in cold-chain to NPRC (Nicholas Piramal Research Center, Mumbai). On receipt, samples were immediately processed for PBL (peripheral blood lymphocytes) isolation by density gradient centrifugation by Ficoll/Hapaque method. The buffy-coat obtained by ficol was washed in RPMI-1640 medium twice. Cells were resuspended in medium containing 10% FBS and GM-CSF at concentration of 0.02-0.08 ng/mL.

Cells obtained were seeded in tissue culture flask and kept in 5% $CO_2$ incubator at 37° C. for 1-2 h for conditioning. Cells after 2 h of incubation were counted on hemocytometer and seeded in 96 well plate at density of $1-5\times10^4$ cells per well in 0.180 mL medium. The compound (extract/imatinib) was diluted to 10× stock and 0.02 mL of these stocks was introduced into wells in triplicates. These plates were further incubated at 37° C. in 5% $CO_2$ incubator. Plates meant for trypan blue cell counting were analyzed every 24 h interval upto 96 h. Plates kept for $^3H$ Thymidine uptake were subjected to thymidine incorporation. The results of this study are presented in the following Table 7.

TABLE 7

Effect of the extract of *Piper betle* leaves on imatinib-resistant CML patient sample

| Sr No | Sample | $IC_{50}$ |
|---|---|---|
| 1 | The extract of *Piper betle* leaves | 18 μg/mL |
| 2 | Imatinib | 8 μM |

Example 9

In-Vivo Efficacy Testing of the Extract of *Piper betle* Leaves in Imatinib-Resistant and Imatinib-Sensitive Tumor Models Cell lines Ba/F3 transfectants expressing full-length wild type Bcr-Abl or mutated Bcr-Abl T315I are used in this study. These are recombinant cell lines procured from Dr. Brian Druker's laboratory, Howard Hughes Medical Institute, Oregon Health and Science University Cancer Institute, Portland, Oreg., USA.

Extract Storage

All the samples (extract/imatinib) were stored at 4-8° C. in an amber coloured bottle. The samples (the extract/imatinib) in solution were also maintained at 4-8° C. in a refrigerator. Sample for animal injection was made fresh every day, residual volume were pooled and discarded as per SOP for chemical disposals.

Dose Preparation

The sample (extract/imatinib) was weighed and admixed with 0.5% (w/v) carboxymethylcellulose (CMC) and triturated with Tween-20 (secundum artum) with gradual addition of water to make up the final concentration.

Efficacy Study in SCID Mice

A group of 85 Severely Combined Immune-Deficient (SCID strain-CBySmn.CB17-Prkdc$^{scid}$/J, The Jackson Laboratory, Stock # 001803) male mice, 6-8 weeks old, weighing ~20 g were used.

BAF3 Bcr-Abl/p210WT cells and BAF3 Bcr-Abl/T315I cells were grown in RPMI1640 medium containing 10% fetal calf serum in 5% $CO_2$ incubator at 37° C. Cells were pelleted by centrifugation at 1000-rpm for 10 minutes. Cells were resuspended in saline to get a count of $80-100\times10^6$ cells per mL, 0.2 mL of this cell suspension was injected by subcutaneous (s.c.) route in SCID mice. Mice were observed every alternate day for palpable tumor mass. Once the tumor size reached a size of 5-7 mm in diameter, animals were randomized into respective treatment groups. Dose was administered every day. Tumor size was recorded at every 2-5 day interval. Tumor weight (mg) was estimated according to the formula for a prolate ellipsoid: {Length (mm)×[width (mm)$^2$]×0.5} assuming specific gravity to be one and π to be three. Tumor growth in compound treated animals was calculated as T/C (Treated/Control)×100% and Growth inhibition Percent (GI %) was [100−T/C %].

Respective treatment groups are presented in the following Table 8.

TABLE 8

Treatment groups (Set I and Set II)

Figure 3B:
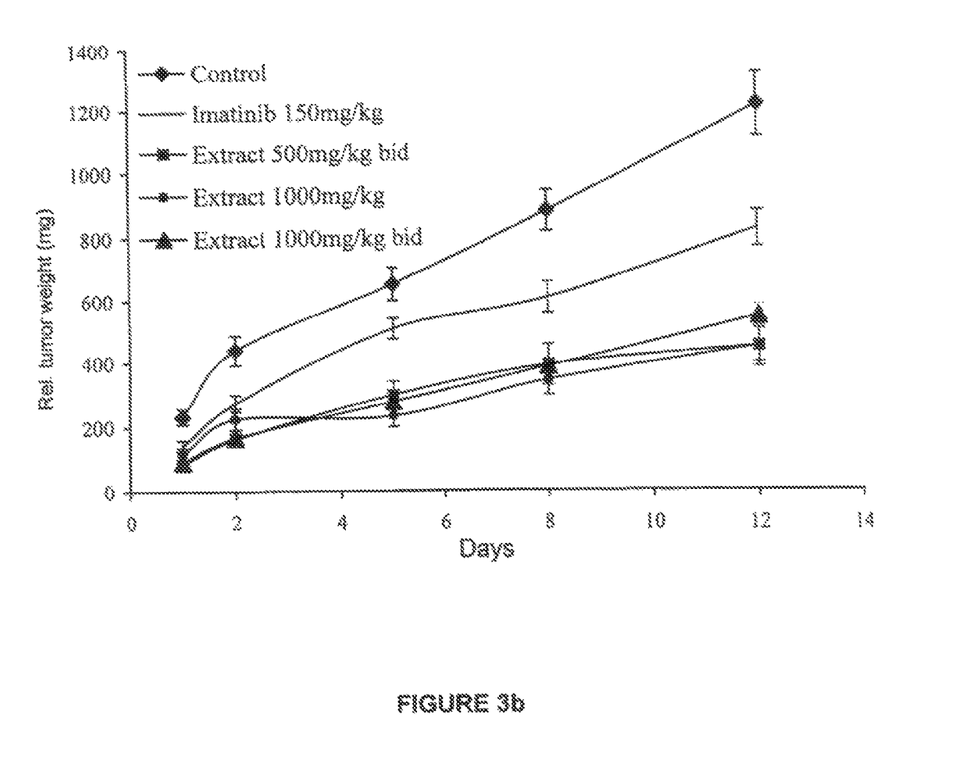
FIG. 3b illustrates that the extract of *Piper betle* leaves exhibits greater in vivo efficacy than imatinib in inhibiting the most predominant mutated form of Bcr-Abl i.e. the Ba/F3 Bcr-Abl/T315I xenograft model in SCID mice (SET II).

| Groups | Sample | Dose | Route | No. of treatments | n = |
|---|---|---|---|---|---|
| (SET I) Designation: Ba/F3 Bcr-Abl/P210 WT | | | | | |
| I | Control (Untreated) | — | p.o. | q1d × 13 | 11 |
| II | Extract of *Piper betle* leaves | 500 mg/kg | p.o. | q1d × 13 | 11 |
| III | Extract of *Piper betle* leaves | 500 mg/kg bid | p.o. | q1d × 13 | 11 |
| IV | Imatinib | 150 mg/kg | p.o. | q1d × 13 | 10 |
| (SET II) Designation: Ba/F3 Bcr-Abl/T315I | | | | | |
| I | Control (Untreated) | — | p.o. | q1d × 11 | 7 |
| II | Extract of *Piper betle* leaves | 500 mg/kg | p.o. | q1d × 11 | 9 |
| III | Extract of *Piper betle* leaves | 500 mg/kg bid | p.o. | q1d × 11 | 9 |
| IV | Extract of *Piper betle* leaves | 1000 mg/kg bid | p.o. | q1d × 11 | 9 |
| V | Imatinib | 150 mg/kg | p.o | q1d × 11 | 8 | p.o. = per oral
q1d × 13 = single administration for 13 days
n = number of animals
Injection volume 10 mL/kg body weight The data presented in the following Table 9 demonstrates that the extract of *Piper belle* leaves exhibits significantly greater in vivo efficacy than imatinib in inhibiting the most predominant mutated form of Bcr-Abl i.e. T315I when tested at the same doses as that of wild type Bcr-Abl expressing xenograft i.e. BAF3 Bcr-Abl/p210 WT. These results are graphically presented in FIGS. 3*a* (SET I) and 3*b* (SET II).

TABLE 9

Growth Inhibition Percent (GI %) (Set I and Set II)

| (SET I) Designation: Ba/F3 Bcr-Abl/p210 WT | | | |
|---|---|---|---|
| Days | Gr. II Extract of *Piper betle* 500 mg/kg | Gr. III Extract of *Piper betle* 500 mg/kg bid | Gr. IV Imatinib 150 mg/kg |
| 6 | 6 | 17 | −1 |
| 8 | 33 | 39 | 39 |
| 10 | 44 | 54 | 56 |
| 14 | 50 | 63 | 61 |
| (SET II) Designation: Ba/F3 Bcr-Abl/T315I | | | | |
| Days | Gr. II Extract of *Piper betle* 500 mg/kg | Gr. III Extract of *Piper betle* 500 mg/kg bid | Gr. IV Extract of *Piper betle* 1000 mg/kg bid | Gr. V Imatinib 150 mg/kg |
| 2 | 63 | 49 | 62 | 38 |
| 5 | 54 | 64 | 58 | 22 |

TABLE 9-continued

Growth Inhibition Percent (GI %) (Set I and Set II)

| 8 | 55 | 61 | 56 | 31 |
| 12 | 62 | 62 | 55 | 32 |

Drug active GI % ≧ 50%
Drug very active GI % > 75%
Drug inactive GI % < 50%
(Values highlighted show significant tumor inhibition)

According to the present invention, the inventors considered the compounds showing % growth inhibition (GI)>50% as active compounds; those showing % growth inhibition (GI)>75% as very active compounds and those exhibiting less than 50% growth inhibition as inactive compounds.

We claim:

1. A method for treating imatinib-resistant chronic myeloid leukemia in a patient comprising administering to the patient a composition comprising a therapeutically effective amount of an extract of *Piper betle* leaves as an active ingredient either alone or with at least one pharmaceutically acceptable excipient, wherein, in the imatinib-resistant chronic myeloid leukemia, in the patient the resistance to imatinib is caused by Bcr-Abl mutation.

2. The method according to claim 1, wherein said extract is administered orally, parenterally, subcutaneously, intravenously or intraarticularly.

3. The method according to claim 2, wherein said extract is administered orally.

4. The method according to claim 3, wherein said extract is formulated in the form of a tablet, capsule, granule, syrup or suspension.

5. The method according to claim 2, wherein said extract is administered parenterally.

6. The method according to claim 1, wherein the extract is administered in a dosage ranging from about 1 g to about 20 g per day.

7. The method according to claim 1, wherein said composition comprises about 5% to about 50% (w/w) of the extract of *Piper betle* leaves.

* * * * *